United States Patent [19]
Malech et al.

[11] Patent Number: 5,593,966
[45] Date of Patent: Jan. 14, 1997

[54] PEPTIDE DERIVATIVES OF CYTOCHROME $B_{558}$ AND THEIR USE AS MEDICAMENTS

[75] Inventors: Harry L. Malech, Bethesda; Daniel Rotrosen, Takoma Park, both of Md.

[73] Assignee: The United States of America as represented by the Department of Health and Human Services, Washington, D.C.

[21] Appl. No.: 527,767

[22] Filed: May 24, 1990

Related U.S. Application Data

[63] Continuation-in-part of Ser. No. 331,652, Mar. 31, 1989, Pat. No. 5,585,346.
[51] Int. Cl.$^6$ .............................. A61K 38/00; C07K 7/00; C07K 7/06
[52] U.S. Cl. .............................. 514/16; 530/329
[58] Field of Search .............................. 530/329; 514/16

[56] References Cited

PUBLICATIONS

Royer-Pokora, et al, "Cloning the gene for an inherited human disorder—chronic granulomatous disease—on the basis of its chromosomal location", Nature, vol. 322, beginning at p. 32, 1986.

Pember, et al., "Cytochrome $b_{558}$ from (Bovine) Ganulocytes" vol. 259, J. Biol. Chem. pp. 10590–10595, 1984.

Lutter, et al., "Purification and Partial Characterization of the b–type Cytochrome from Human Polymorphonuclear Leukocytes", J. Biol. Chem. vol. 260 (4) pp. 2237–2244, 1985.

Parko's et al, "Purified Cytochrome b from Human Granulocyte Plasma Membrane is comprised of two polypeptide with Relative Molecular Weights of 91,000 and 22,000". J. Clinc. Invest, vol. 80, pp. 732–742.

Iizuka et al. "Pyridine and Imidazole Reversibly inhibit the Respiratory Burst of Porcine and Human Neutrophils" Biochem and Biophysic Res Comm. vol. 130 (2) pp. 621–626.

Kleinberg, et al, "Glycosylation of Cytochrome $b_{558}$ Large Subunit Varies in Different Human Phagocytic Cells", vol. 143, pp. 4152–4157, 1989.

Yamaguchi, et al., "Purification and some Properties of the Small Subunit of Cytochrome $b_{558}$ from Neutrophils", J. Biol. Chem., vol. 261 (1) pp. 112–118, 1989.

Verhoeven et al, "Characterization of two monoclonal antibodies against Cytochrome $b_{558}$ of Human Neutrophils" Blood vol. 73, (6) pp. 1686–1694, 1989.

Rotrosen, et al, J. Biol. Chem. vol. 265, No. 32, pp. 1910–19915, 1990.

Levy, et al, Biochem and Biophysc Res. Comm vol. 170, 3, 1114–11120.

Rotrosen et al, J. Biol. Chem, vol. 265, 15, pp. 8745–8750, 1990.

Kleinberg, et al, Biochemistry 31, pp. 2686–2690, 1992.

Kleinberg, et al, J. Biol. Chem vol. 265, 26, pp. 15577–15583, 1990.

Grynkiewicz, et al, J. Biol. Chem, vol. 260, pp. 3440–3450 1989.

Rostrosen, et al, I "A cytoplasmic carboxyterminal . . . " Clin. Res. vol. 36, No. 3, 1988.

Rostrosen et al II "Evidence for interaction . . . ," Clin. Res. vol. 37, No. 2, 1989.

Royer–Pokora, et al, "Cloning the gene for an inherited human disorder, . . . ", Nature 322:32, 1986

*Primary Examiner*—Elizabeth C. Weimar
*Assistant Examiner*—S. G. Marshall
*Attorney, Agent, or Firm*—Birch, Stewart, Kolasch & Birch, LLP

[57] ABSTRACT

Peptide derivatives with inhibitory activity on the enzyme systems involved in the oxidative burst of human phagocytic cells comprise six and seven amino acid peptide sequences from human cytochrome $b_{558}$. The derivatives may be used in medicaments for the treatment of inflammatory diseases.

13 Claims, 4 Drawing Sheets

PEPTIDE DERIVATIVES OF CYTOCHROME $B_{558}$ AND THEIR USE AS MEDICAMENTS

CROSS REFERENCE RELATED APPLICATIONS

This application is a Continuation-In-Part of application Ser. No. 07/331,652 filed on Mar. 31, 1989, now U.S. Pat. No. 5,585,346, the entire contents of which are hereby incorporated by reference.

BACKGROUND OF THE INVENTION

1. Field of the Invention

The present invention relates to peptide derivatives having six and seven amino acid peptide sequences with inhibitory activity on the enzyme systems involved in the oxidative burst of human phagocytic cells. More specifically, the invention relates to peptide derivatives comprising a limited number of carboxylterminal amino acids of human cytochrome $b_{558}$ which appear to inhibit activation of the respiratory burst of human phagocytic cells, i.e. neutrophils, eosinophils and monocytes. The peptide derivatives are foreseen to be used in medicaments for mammals, including humans, in the treatment of inflammatory diseases.

2. Description of the Technical Background

A large number of anti-inflammatory drugs have been devised which either decrease the accumulation of phagocytic cells at sites of inflammation or decrease the level of activation of phagocytic cells. Such substances include corticosteroids which act on the overall metabolism of cells or nonsteroidal anti-inflammatory drugs such as aspirin, ibuprofen, indomethacin and others which interfere with the metabolism of arachidonic acid. As a result of these actions, they interfere with the accumulation and activation of phagocytic cells. These substances do not have any specificity for phagocytic cells or the functions of phagocytic cells, and the side effects of these agents relate in part to actions on other cell types and organ systems.

SUMMARY OF THE INVENTION

One purpose of this invention is to devise an anti-inflammation substance which would act in a highly specific fashion to inhibit the production of toxic oxygen products (superoxide, hydrogen peroxide, hydroxyl radical and others) by human phagocytic cells and thereby decrease the tissue damage which occurs at sites of inflammation as a result of the action of these oxidative products. An inhibitor whose structure is determined by knowledge of the structure and function of components of the superoxide producing system of human phagocytes is likely to inhibit this system without affecting other phagocytic cell activities or the function of other cell types or organ systems.

It has now, in accordance with the invention, been found that two certain sequences of a number of carboxyl-terminal amino acids of human cytochrome $b_{558}$ (a component of the oxidative burst enzyme system) appear to inhibit activation of the respiratory burst of the human neutrophil, monocyte and eosinophil. These six and seven amino acid sequences constituting the peptide derivative compete with native cytochrome $b_{558}$ for binding to other enzymatic components of the phagocytic cell superoxide producing system and thereby prevent activation of NADPH oxidase activity critical to superoxide production. Hence, the invention relates to optionally substituted peptide derivatives which block superoxide production in phagocytic cells, containing six to seven amino acid residues and containing a domain which is identical to a domain of the 91 kDa subunit of human cytochrome $b_{558}$. It is preferred that the peptides contain either the amino acid sequence Arg—Gly—Val—His—Phe—Ile or the amino acid sequence Arg—Gly—Val—His—Phe—Ile—Phe, which sequences are identical to a domain of the carboxyl-terminal peptide position of the 91 kDa subunit of human cytochrome $b_{558}$.

DETAILED DESCRIPTION OF THE INVENTION

Figure 1A:
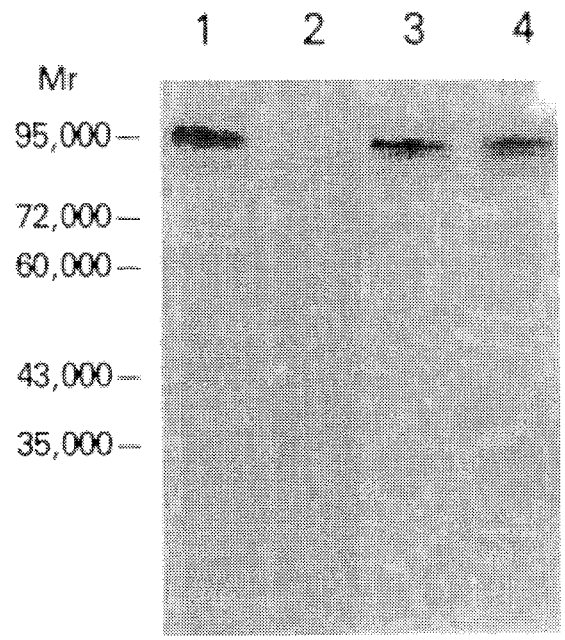
FIG. 1(A) shows the results of analysis by SDS-PAGE and immunoblotting which indicate that antiserum directed against cytochrome $b_{558}$ large subunit carboxyterminus specifically recognizes a 91 kDa PMN protein.

The present invention relates to optionally substituted peptide derivatives which block superoxide production in phagocytic cells, containing six to seven amino acid residues and containing a domain which is identical to a domain of the 91 kDa subunit of human cytochrome $b_{558}$. It is preferred that the peptides contain either the amino acid sequence Arg—Gly—Val—His—Phe—Ile or the amino acid sequence Arg—Gly—Val—His—Phe—Ile—Phe, which sequences are identical to a domain of the carboxyl-terminal peptide position of the 91 kDa subunit of human cytochrome $b_{558}$.

It is contemplated that addition of a certain class of chemical moieties selected from the groups comprising hydrophobic and amphipathic groups will enhance the penetration of the peptide derivatives into phagocytic cells and/or will assist in the retention of such substituted derivatives of the peptides within phagocytic cells. Examples of such auxiliary groups are cleavable ester groups such as acetoxymethylester which has been used successfully to modify hydrophilic, ionic chemical substances which then may pass through the lipid barrier of the cell exterior and into the inside of living human cells and tissues (Grynkeiwicz G, Poenie M, and Tsien R. The Journal of Biological Chemistry 1985 Mar. 25, 260;3440–3450, 1985). When the derivatives are to be used in warm-blooded animals including human beings, it is appreciated that the derivatization should not render the peptide derivatives toxic. Peptide derivatives with added chemical moieties as defined above are pro-drugs for the active peptide derivatives.

It is contemplated that the mechanism of action is to directly inhibit activation of the specific enzymes involved in the oxidative burst of human phagocytic cells, by binding to critical components of this system within phagocytic cells. Because of this mechanism of action it is contemplated that the peptide derivatives comprising the carboxyl-terminal domain of cytochrome $b_{558}$ will act only on phagocytic cells and specifically decrease production of toxic oxygen products by these cells with a minimum of effects upon other cell types and organ systems.

The mode of action is probably due to a condition in which the peptide derivatives according to the invention dominates the native cytochrome $b_{558}$ in binding to other enzymatic components of the phagocytic cell superoxide producing system and thereby prevents activation of NADPH oxidase activity critical to superoxide production.

Hence, another aspect of the invention relates to a method for directly inhibiting activation of the specific enzyme system involved in the oxidative burst of human phagocytic cells which involves administration of an effective amount of an optionally substituted peptide derivatives identical with a domain of the 91 kDa subunit of human cytochrome $b_{558}$ which blocks superoxide production in phagocytic cells.

A further aspect of the invention relates to a method for directly inhibiting activation of the specific enzyme system involved in the oxidative burst of human phagocytic cells which involves administration of an effective amount of optionally substituted peptide derivatives comprising the carboxyl-terminal domain of cytochrome $b_{558}$. The peptide derivatives involved are as described above.

A further aspect of the invention relates to a method for preventing or decreasing the tissue damage associated with phagocyte oxidative burst which involves administration of an optionally substituted peptide derivative as described above. The invention relates specifically to a method for preventing or decreasing symptoms such as gout, autoimmune disorders, myocardial infarction, adult respiratory distress syndrome, asthma and certain dermatological disorders which comprises administering an effective amount of the peptide derivative thereof to a patient in need of such treatment.

A further aspect of the invention relates to a medicament comprising the optionally substituted peptide derivatives as described above.

The medicaments according to the invention can be prepared by methods well known in pharmaceutical practice.

The peptide derivatives according to the invention can be formulated into forms for administration to mucous membranes, intraarticular forms for administration into joints, topical cutaneous administration forms such as ointments, solutions, creams and lotions, parenteral preparations such as dispersions and solutions, and inserts such as suppositories; together with suitable carriers, excipients, binders, fillers, etc., into dosage forms each comprising a fraction or a multiplum of the daily dose required in order to achieve the desired result of treatment. While oral delivery may be effective, local delivery of peptide in a carrier to sites of inflammation may be preferred (droplet as nebulization of peptide in aqueous or organic carrier [such as dimethyl sulfoxide] for application to mucous membranes or inhalation to lungs; external local application of peptide in aqueous or organic carrier; or injection of peptide in solvent carrier to joints or other sites). For such local application the peptides may be present in carrier at concentrations of 0.01 to 1.0 mg/ml, optimally at 0.1 mg/ml. For injection directly into a joint in a human an indicated daily dose lies in the range of 0.1–3 mg of peptide derivative, preferably 0.5–2.0 mg; said dose can be given in 1–2 ml of carrier. Intravenous delivery of peptide may be required for systemic treatment. For such systemic treatment the amount of active ingredient in each administration form lies between 0.1 and 1 g which may be given in preparations comprising between 1 and 95% by weight of the active ingredient, the balance being the auxiliary agent(s).

Liquid administration forms may be prepared from concentrated forms by adding physiologically acceptable carriers or diluents such as water, saline, glucose solutions, etc., optionally comprising buffering agents and salts rendering the final liquid preparation isotonic.

The peptide may also be incorporated into liposomal vesicles exactly as described for incorporating the antibiotic amphotericin B into lipid vesicles (e.g. as described in the references: Lopez-Berenstein, G., Fainstein, V., Hopfer, R., Mehta K., Sullivan, M. P., Keating, M., Rosenblum, M. G., Mehta, R., Luna, M., Hersh, E. M., Reuben, J., Juliano, R. L., Bodey, G. P. (1985) Liposomal amphotericin B for the treatment of systemic fungal infections in patients with cancer: A preliminary study. *J. Infec. Dis.* 151:704–710; Lopez-Berestein, G. (1987) Liposomes as carriers of antimicrobial agents. *Antimicrob. Agents Chemother.* 31:675–678; Lopez-Berestein, G., Hopfer, R. L., Mehta, R., Mehta, K., Hersh, E. M., Juliano, R. L. (1984) Liposome-encapsulated amphotericin B for the treatment of disseminated candidiasis in neutropenic mice. *J. Infect. Dis.* 150:278–283; and Mehta, R., Lopez-Berestein, G., Hopfer, R., Mills, K., Juliano, R. L. (1984) Liposomal amphotericin B is toxic to fungal cells but not to mammalian cells. *Biochem. Biophys. Acta* 770:230–234). The amount of peptide incorporated into liposomes may be 0.1 mg peptide to 1 mg peptide per mg lipid. The amount of peptide administered in lipid encapsulated form will be identical to the injection route doses indicated above.

The peptide derivatives can be prepared as described in the literature (Lifson J. D., Hwang K. M., Nara P. L., Fraser B., Padgett M., Dunlop N. M., Eiden L. E. Synthetic CD4 peptide derivatives that inhibit HIV infection and cytopathicity, Science 1988 Aug. 5;241 (4866):712–6; Lindner W, Robey F. A. Automated synthesis and use of N-chloroacetyl-modified peptides for the preparation of synthetic peptide polymers and peptide-protein immunogens. Int J Pept Protein Res 1987 Dec;30(6):794–800; Barany G., Kneib-Cordonier N., Mullen D. G. Solid-phase peptide synthesis: a silver anniversary report. Int J Pept Protein Res 1987 Dec;30(6):705–39; Clark-Lewis I, Aebersold R., Ziltener H., Schrader J. W., Hood L. E., Kent S.B. Automated chemical synthesis of a protein growth factor for hemopoietic cells, interleukin-3. Science 1986 Jan 10; 231 (4734):134–9).

In particular, the peptides were synthesized using an Applied Biosystems 430A Automated Synthesizer following manufacturer's instructions. Synthesized peptides were cleaved from the resin and deblocked using hydrofluoric acid following standard procedure as indicated above. After neutralization with sodium hydroxide to pH 7, the peptides were dialyzed into ammonium carbonate buffer and then lyophilized. Sequence was confirmed by peptide composition analysis.

The invention is illustrated in the Examples below, but it should be understood that the detailed description and specific examples, while indicating preferred embodiments of the invention, are given by way of illustration only, since various changes and modifications within the spirit and scope of the invention will become apparent to those skilled in the art from the detailed description.

In the present specification, claims and Examples the following abbreviations of the amino acids are used:

A=Ala=Alanine
R=Arg=Arginine
N=Asn=Asparagine
D=Asp=Aspartate
C=Cys=Cysteine
Q=Gln=Glutamine
E=Glu=Glutamate
G=Gly=Glycine
H=His=Histidine
I=Ile=Isoleucine
L=Leu=Leucine
K=Lys=Lysine
M=Met=Methionine
F=Phe=Phenylalanine
P=Pro=Proline
S=Ser=Serine
T=Thr=Threonine
W=Trp=Tryptophan
Y=Tyr=Tyrosine
V=Val=Valine

EXAMPLES

Cell-Free NADPH Oxidase Assay

Neutrophils were isolated from peripheral blood and cytosol and membrane fractions were prepared by differential centrifugation as previously described (Nunoi et al, *Science*, 242, 1298–1301 (1988)). Typical yields of cytosol and membrane proteins obtained were $2.8\pm0.1$ mg/$10^8$ cell equivalents and $1.5\pm0.1$ µg/$10^6$ cell equivalents, respectively (mean±SD, 3 separate preparations). The cell-free assay of $O_2$ generation was modified as follows: wells contained $2.5–5.0\times10^5$ cell equivalents neutrophil membrane, $10^6$ cell equivalents neutrophil cytosol in a final volume of 100 µl reaction mixture (150 µM acetylated ferricytochrome c (11), 4 mM $MgCl_2$, 10 µM FAD, 1 mM EGTA, 200 µM NADPH, 40 µM arachidonic acid, 10 µM $GTP_\gamma S$, ±25 µg/ml superoxide dismutase in 75 mM potassium phosphate, pH 7.0). Because membrane preparations varied in activity, the amount of membrane added per well was adjusted to yield an arachidonate-stimulated $O_2$ production of $\approx 0.4$ nmol/min/well in the absence of synthetic peptide. The maximal linear rate of superoxide dismutase-inhibitable acetylferricytochrome c reduction ($\Delta$O.D. 500 nm) was converted to nmol $O_2$ generated/min using an instrument-corrected extinction coefficient derived empirically as described (Leslie, J. Immunol. Methods, 103, 253–259 (1987)). To measure oxidase inhibition by antibodies directed against the 91 kDa subunit of cytochrome $b_{558}$ membranes were solubilized in 1% deoxycholate, incubated for 30 min on ice with an equal volume of serum at various dilutions. Diluting these samples 10-fold with $H_2O$ lowered the detergent concentration below the CMC and allowed sedimentation (130,000 g×30 min) of an oxidase-competent membrane fraction. This fraction was resolubilized in deoxycholate, and assayed for arachidonate-stimulated $O_2$ generation in the presence of cytosol.

Permeabilized Cell NADPH Oxidase Assay

Neutrophils were electropermeabilized as described (Grinstein et al, J. Biol. Chem., 263, 1779–1783 (1988)), incubated on ice for 30 min in permeabilization buffer (140 mM KCl, 1 mM $MgCl_2$, 1 mM EGTA, 0.193 mM $CaCl_2$, 1 mM ATP, 2 mM NADPH, 10 µM GTP, 10 mM glucose, 10 mM HEPES-N-methylglucamine, pH 7) supplemented with synthetic peptide (800 µM). The cells were resuspended at $5\times10^6$/ml in the same buffer containing 200 µM synthetic peptide, 150 µM acetylferricytochrome c, catalase (2500 U/ml), ±25 µg/ml superoxide dismutase. Wells containing $5\times10^5$ cells were stimulated with PMA (10 ng/ml) or fMLP (10 µM) and $O_2^-$ production was determined as above. Superoxide production by intact PMN was not significantly altered by synthetic peptides at extracellular peptide concentrations $\leq 200$ µM.

Immunoblotting and Immunofluorescence

Neutrophil 0.1% Triton X-100 extracts ($5\times10^6$ cell equivalents/lane) were analyzed by SDS-PAGE and immunoblotting (Rotrosen et al, J. Biol. Chem., 263, 10958–10964 (1988); Kleinberg et al, J. Immunol. (in press) (1988)). The primary antibody was a 1:50 dilution of serum from rabbits immunized with KLH-conjugated synthetic peptide (CSNPRGVHFIFNKENF), which includes residues 558–570 (bolded) of 91 kDa cytochrome b558. For immunochemical localization of the 91 kDa subunit carboxyterminus neutrophils were plated in tissue culture dishes and were exposed to phorbol myristate acetate (PMA, 1 µg/ml, 2 min) to promote translocation of intracellular cytochrome reserves to the plasma membrane. The cells were stained intact or after shearing in a stream of relaxation buffer directed perpendicular to the monolayer by a dental water pik. The firmly attached membrane patches with cytoplasmic face exposed conformed to the "footprints" of the intact neutrophils before shearing. Membrane patches were devoid of phase dense or darkfield visible structures (e.g., granules). The presence of membrane patches adherent to the plates after shearing was confirmed by fluorescence microscopy using the lipophilic dye, di-S-C3, and by electron microscopy. Intact neutrophils and membrane patches of sheared neutrophils were incubated at 4° C. with preimmune serum or rabbit antiserum raised against 91 kDa cytochrome b558 carboxyterminal synthetic peptide (1:200 in PBS containing 2 mg/ml normal goat IgG), stained with Texas red-conjugated goat anti-rabbit IgG (1:200 in PBS), and photographed at identical exposure settings for all conditions. Fluorescence was negligible on membrane patches of normal neutrophils stained with preimmune serum or with anti-91 kDa cytochrome b558 serum in the presence of 50 µM synthetic peptide (not shown).

Synthetic Peptides

Peptides were synthesized by OCS Laboratories (Denton, Tex.) or by the Biologic Resources Branch, NIAID. Peptides were used for immunization and in functional studies as synthesized. Synthetic peptides were separated on a Vydac (Hesperia, Calif.) C-18 reverse phase column by elution with $H_2O/0.1\%$ TFA and $CH_3CN/0.1\%$ TFA gradients. The inhibitory RGVHFIF-containing peptides ranged from 64–70% homogeneous by HPLC. The inhibitory peptide RGVHFIF contained the correct ratio of amino acids by compositional analysis and yielded the correct amino acid sequence from the major peak purified by HPLC.

47 kDa Cytosolic Protein Phosphorylation

Components of the cell-free phosphorylation reaction were identical to those for arachidonate-stimulated $O_2^-$ generation except for omission of acetylferricytochrome c and inclusion of $\gamma$-[$^{32}$P]ATP (0.1 µCi/ml, sp. act. 5000 Ci/mmol). Twenty min after addition of arachidonate, aliquots of the cell-free reaction mixture were mixed with an equal volume of iced "stopping" buffer (150 mM NaCl, 10 mM EDTA, 1% deoxycholate, 1% NP-40, 50 mMNaF, 1 mMNa vanadate, 10 mM Tris, pH 7.4). Proteins bound to rabbit antibodies raised against recombinant 47 kDa protein (Lomax et al, Science, 245, 409–412 (1989)), were precipitated with protein G-sepharose (Harlow et al, Antibodies: A Laboratory Manual (Cold Spring Harbor Laboratory), 465–468 (1988)) and analyzed by SDS-PAGE and autoradiography with intensifying screens.

Results

FIG. 1(A) shows that antiserum directed against cytochrome b558 large subunit carboxyterminus specifically recognizes a 91 kDa PMN protein analyzed by SDS-PAGE and immunoblotting. Lanes 1 and 3, normal PMN; land 2, X-linked CGD, cytochrome b558-deficient PMN; land 4, autosomal recessive CGD, cytochrome b558-positive PMN.

Figure 1B:
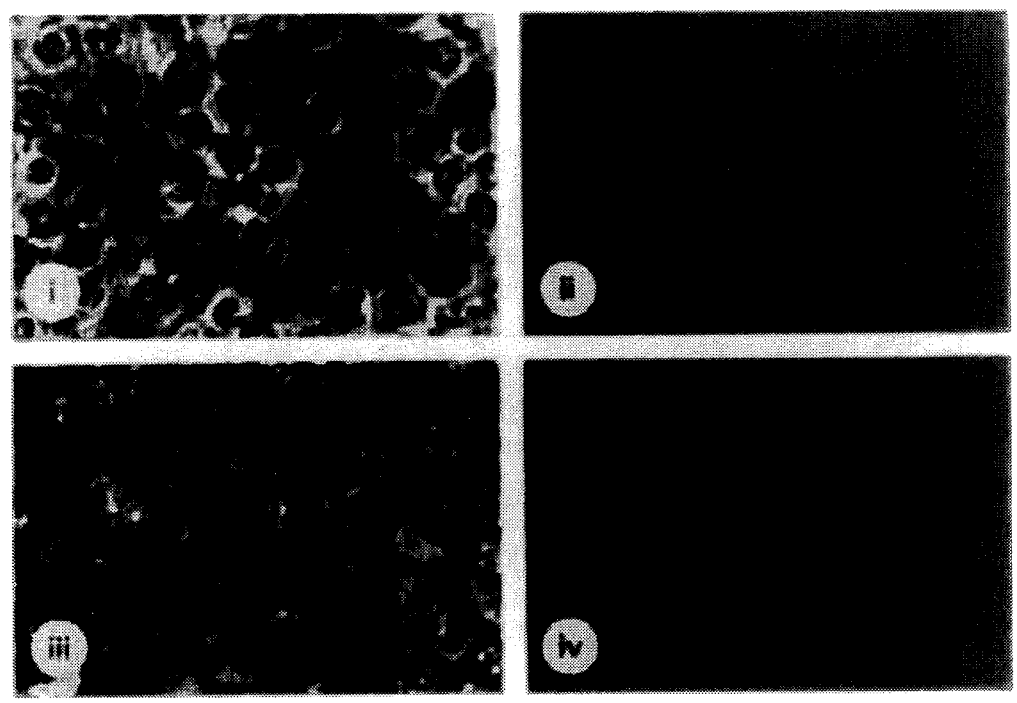
FIG. 1(B) shows the results of immunofluorescence microscopy which detects epitopes of 91 kDa cytochrome $b_{558}$ exclusively on the cytoplasmic face of PMN plasma membranes.

FIG. 1(B) shows the results of indirect immunofluorescence microscopy which detects epitopes of 91 kDa cytochrome b558 exclusively on the cytoplasmic face of PMN plasma membranes. i, phase contrast, intact PMN; ii–iv, fluorescence microscopy after staining with anti-91 kDa cytochrome b558: ii, intact PMN; iii, sheared normal PMN; iv, sheared X-linked CGD cytochrome b558-deficient PMN. PMN plasma membrane sheets were prepared as described above. The transmembrane orientation of cytoplasmic epitopes in these membrane patches was independently confirmed using antisera directed against G-protein α-subunits, membrane-associated proteins which lack extracellular domains (not shown).

Thus, synthetic peptide antiserum raised against a carboxyterminal region of the large subunit of cytochrome b558 detected a 91 kDa protein on SDS-PAGE immunoblots of detergent extracts of normal, but not X-linked CGD neutrophils (FIG. 1(A)). Thus, the same antiserum as employed in the immunoblots of FIG. 1(A) did not bind to the extracellular surface of intact neutrophils, but bound to the cytoplasmic surface of membrane patches from sheared normal neutrophils (FIG. 1(B)). In contrast, this antiserum did not bind to membranes of sheared neutrophils from patients with X-linked CGD who lack cytochrome b558 (FIG. 1(B)). These observations indicate that binding of this antiserum is specific for the 91 kDa subunit of cytochrome b558 and that the epitopes recognized by the antiserum are exposed at the cytoplasmic face of the plasma membrane.

Reconstitution of NADPH oxidase in an amphiphile activated broken-cell system, requires phagocyte membranes and cytosol. Incubation of neutrophil membranes with antiserum directed against the carboxyterminus of the 91 kDa subunit of cytochrome b558 blocked NADPH oxidase activity in this cell-free system in a specific and concentration-dependent fashion (as evidenced by the results in FIG. 2(A)).

Figure 2A:
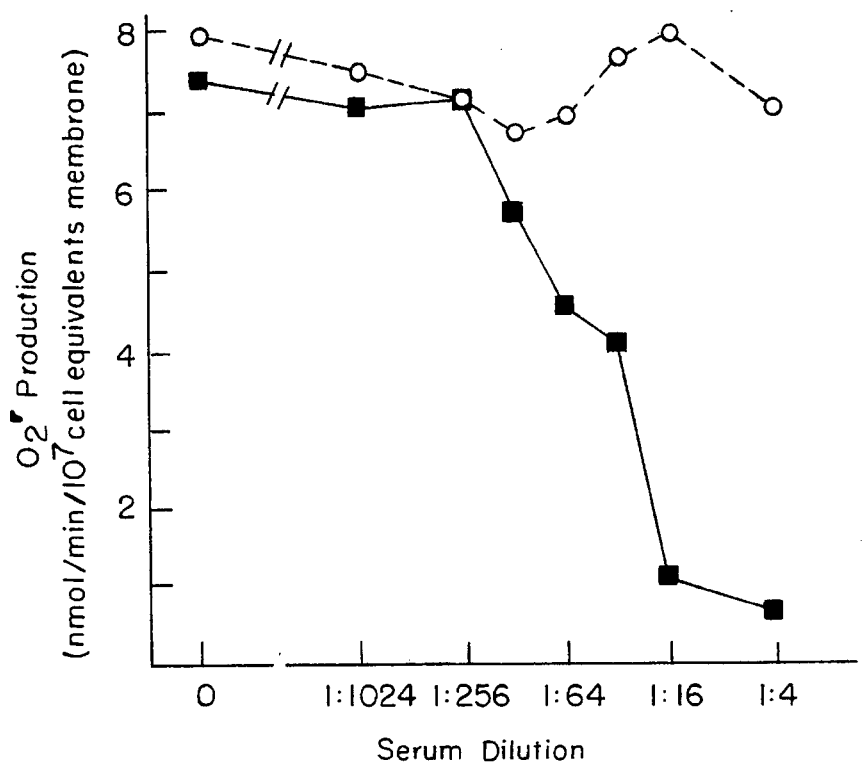
FIG. 2(A) is a graph showing inhibition of NADPH oxidase activation by 91 kDa cytochrome $b_{558}$ by carboxyterminal antiserum or preimmune serum.

FIG. 2(A) is a graph showing inhibition of NADPH oxidase activation by 91 kDa cytochrome b558 carboxyterminal antiserum ■----■, or preimmune serum o----β. PMN membranes were incubated with antisera before measurement of $O_2^-$ production as described above. Inhibition studies were also done with synthetic peptides. Peptides derived from the same carboxyterminal region of the 91 kDa subunit of cytochrome b558 used to raise the antibody and encompassing the sequence RGVHFIF (residues 559–565) inhibited $O_2^-$ production in the cell-free assay. Control peptides of similar size with varied net charge and amphiphilicity were not inhibitory as evidenced by the results below in Table 1.

TABLE 1

| Peptide source | Peptide sequence | Mean inhibition vs. buffer control (n) | | |
| --- | --- | --- | --- | --- |
| | | Cell-free assay | Electropermeabilized cell | |
| | | | PMA | FMLP |
| Cytochrome b β-subunit | | | | |
| Residues 552–570 | SNSESGPRGVHFIFNKENF | 96 (5) | ND* | ND |
| Residues 559–570 | RGVHFIFNKENF | 93 (4) | 61 (2) | 67 (2) |
| Residues 559–565 | RGVHFIF | 97 (2) | 72 (2) | 73 (3) |
| Residues 552–558 | SNSESGP | –8 (4) | –1 (2) | 2 (2) |
| Residues 2–9 | GNWAVNEGC | –17 (2) | ND | ND |
| Residues 119–126 | HLFNVEWC | –17 (2) | –6 (2) | 6 (2) |
| Peptides not derived from cytochrome b | | | | |
| Bradykinin | RPPGFSPFR | –8 (2) | –8 (2) | –6 (2) |
| Control peptide | RKRAHAGFQATI | –5 (3) | –11 (2) | –28 (2) |
| Control peptide | VFSMFQGEES | 10 (2) | 3 (2) | –5 (2) |

*ND = not determined.

In Table 1 above, the cell-free assay of $O_2^-$ generation contained 2.5–5.0×10$^5$ cell equivalents of neutrophil (PMN) membrane, 10$^6$ cell equivalents PMN cytosol in a final volume of 100 µl reaction mixture. Because membrane preparations varied in activity, the amount of membrane added per well was adjusted to yield an arachidonate-stimulated $O_2^-$ production of ≈0.4 nmol/min/well in the absence of synthetic peptide. Data represent the mean percent inhibition obtained in n experiments (each performed in duplicate) in the presence of 100 µM synthetic peptide compared to a simultaneous buffer control. Additional control peptides that did not inhibit $O_2^-$ production at 250 µM included CQTNEENWRVLP, CTTTVMNPKFAES, and CDDSDDDLLHI (not shown in the table).

Electropermeabilized PMN were incubated on ice in permeabilization buffer supplemented with synthetic peptide (800 μM). The cells were resuspended at 5×10⁶/ml in the same buffer containing 200 μM synthetic peptide. Wells containing 5×10⁵ cells were stimulated with PMA (10 ng/ml) or fMLP (10 μM) and $O_2$ production was determined as described in "Experimental Procedures". Superoxide production by intact PMN was not significantly altered by synthetic peptides at extracellular peptide concentrations ≦200 μM. Electropermeabilized PMN sham incubated without synthetic peptides and stimulated with PMN or fMLP generated 8.4±1.1 nmol $O_2$ /min/10⁶ cells and 8.9±1.7 nmol $O_2$ /min/10⁶ cells, respectively (mean±SEM, 5 independent experiments). Electropermeabilized PMN of patients with CGD did not reduce acetylferricytochrome c; n.d., not determined.

Figure 2B:
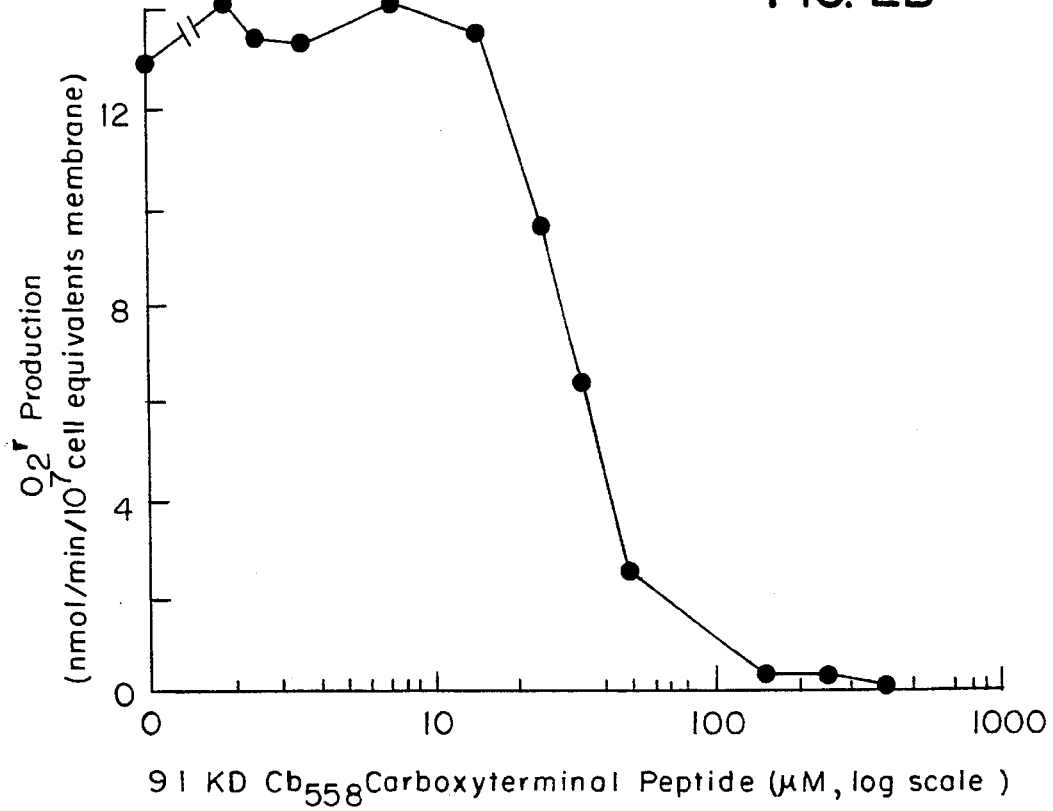
FIG. 2(B) is a graph showing inhibition NADPH oxidase activation by a specific 91 kDa cytochrome $b_{558}$ carboxyterminal peptide.
Figure 2C:
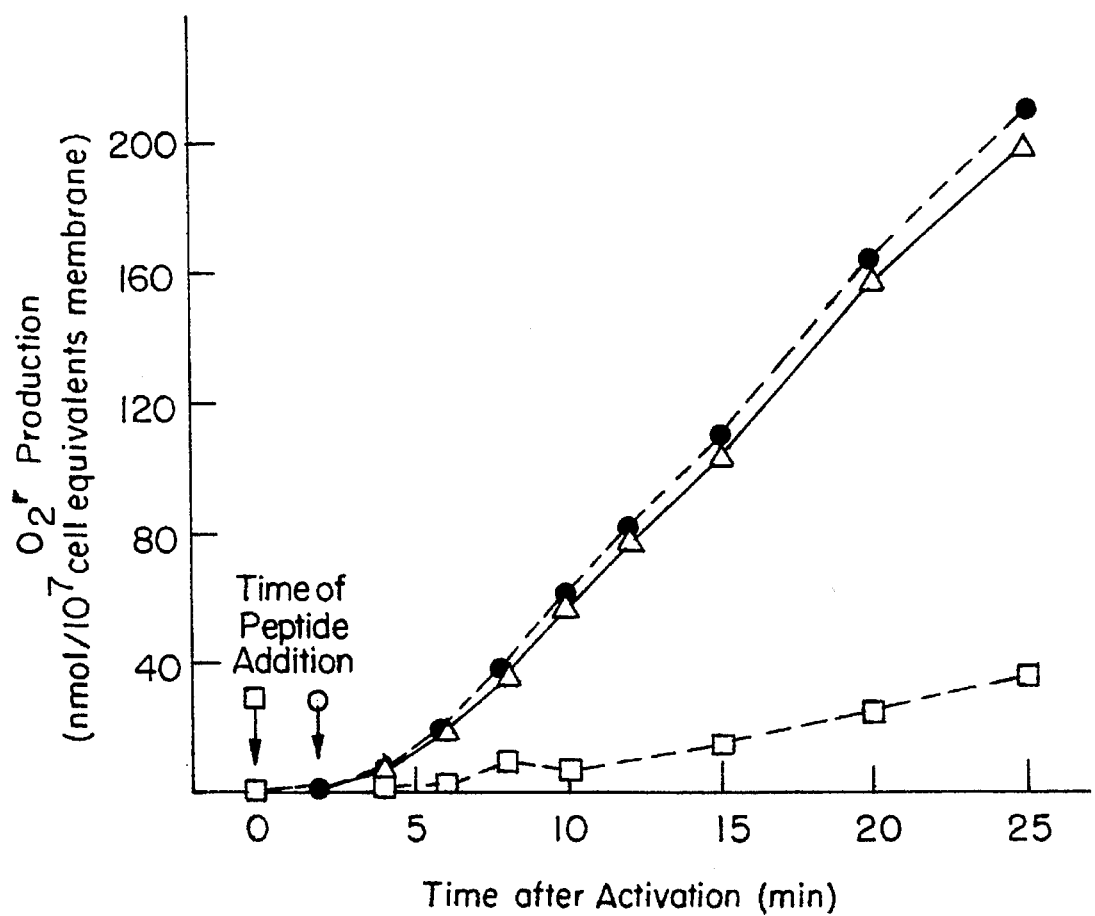
FIG. 2(C) is a graph showing a time course for inhibition of NADPH oxidase activation by 91 kDa cytochrome $b_{558}$ carboxyterminal peptide added with arachidonic acid compared to control without added peptide.

Inhibition by peptide was concentration dependent as evidenced by the graph of FIG. 2(B) which shows inhibition of NADPH oxidase activation by 91 kDa cytochrome b558 carboxyterminal peptide CSNSESGPRGVHFIFNKENF. 91 kDa cytochrome b558 carboxyterminal peptide and arachidonate were added simultaneously. Mean $IC_{50}$±SEM =32±2 μM (5 experiments, $IC_{50}$ determined by interpolation). Inhibition occurred only when peptide was added to the assay before activation by arachidonate as shown by the results graphed in FIG. 2C which show a time course for inhibition of NADPH oxidase activation by 91 kDa cytochrome b558 carboxyterminal peptide added with arachidonic acid (ε----ε) or 2 min after arachidonic acid (o----o), compared to control without added peptide (Δ----Δ). Note that the data in FIGS. 2(A)–2(C) are means of duplicate wells in a single experiment representative of at least 2 experiments performed. Range of duplicates <5% of plotted values. This suggests that the peptide inhibits processes critical to oxidase activation, rather than scavenging $O_2$ or uncoupling the flow of electrons from NADPH to molecular oxygen.

To show that the inhibitory effects of these synthetic peptides were not an artifact of conditions peculiar to the cell-free assay, the effects of these peptides in neutrophils permeabilized by high voltage electrical discharge were tested where oxidase activation pathways may more closely resemble those of the intact cell. Electroporated neutrophils are permeable to small molecules and produce superoxide in response to formyl-methionyl-leucyl-phenylalanine (fMLP) or phorbol myristate acetate (PMA). The small peptides RGVHFIF (MW 875) and RGVHFIFNKENF (MW 1510) inhibited $O_2$ production by electropermeabilized neutrophils stimulated with fMLP or PMA (Table 1). Control peptides matched for size and charge were not inhibitory. The RGVHFIF-containing peptides did not inhibit the respiratory burst of nonpermeabilized neutrophils.

Figure 3A:
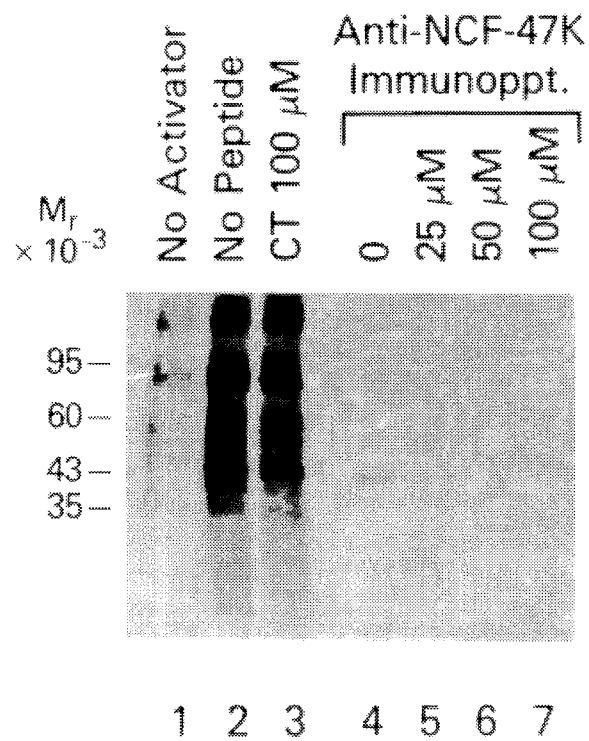
FIGS. 3(A) and 3(B) show the results of immunoprecipitated $^{32}P$ phosphate labelled 47 kDa oxidase proteins which were analyzed by SDS-PAGE and autoradiography, and demonstrate that 91 kDa cytochrome $b_{558}$ carboxyterminal peptide inhibits such phosphorylation critical to oxidation.

After stimulation of the neutrophil respiratory burst with phorbol esters the 47 kDa cytosolic oxidase factor is multiply phosphorylated and associates with plasma membrane. In contrast, in X-linked CGD neutrophils, which lack cytochrome b558 , the 47 kDa cytosolic protein is abnormally phosphorylated and does not associate with membrane. These observations are consistent with a role for cytochrome b558 in regulating phosphorylation and/or membrane association of the 47 kDa protein and provided a rationale for examining the effects of inhibitory cytochrome b558 peptides on phosphorylation of the 47 kDa protein. RGVHFIF-containing peptides inhibited phosphorylation of the 47 kDa protein in the cell-free assay while minimally altering arachidonate-stimulated phosphorylation of other proteins as illustrated in FIG. 3(A) which shows the inhibition of 47 kDa cytosolic protein phosphorylation by 91 kDa cytochrome b558 carboxyterminal peptides. Components of the cell-free phosphorylation reaction were identical to those for arachidonate-stimulated $O_2$ generation except for omission of acetylferricytochrome c and inclusion of [³²P]ATP. Phosphorylated 47 kDa oxidase factor was immunoprecipitated from aliquots of the reaction mixture containing 2.5×10⁵ or 5×10⁵ cell equivalents of cytosol in panel A and B, respectively. The immunoprecipitated proteins were analyzed by SDS-PAGE and autoradiography as described above. The results shown are representative of 3 separate experiments. In FIG. 3(A), lanes 1–3, 5% of total starting material for immunoprecipitation; lane 1, baseline phosphorylation without arachidonate; lane 2, arachidonate-stimulated phosphorylation; lane 3, arachidonate-stimulated phosphorylation in the presence of 100 μM 91 kDa cytochrome b558 carboxyterminal peptide (residue 552–570, CSNSESGPRGVH-FIFNKENF); lane 4–7, immunoprecipitated 47 kDa protein phosphorylated in the presence of arachidonate plus 0, 25, 50, and 100 μM 91 kDa cytochrome b558 carboxyterminal peptide, respectively. The half-maximal inhibitory concentration of 91 kDa cytochrome b558 carboxyterminal peptide determined by densitometry of autoradiograms was in the range of 25–50 μM in each of 3 independent experiments.

Figure 3B:
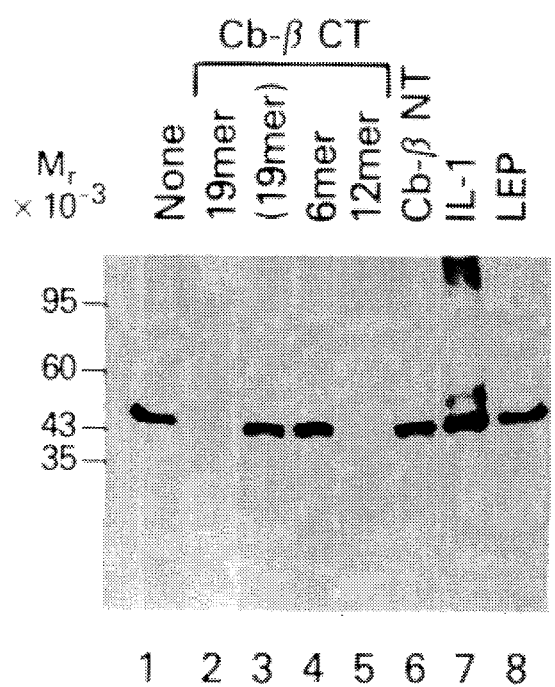

Control peptides did not inhibit phosphorylation of the 47 kDa protein as illustrated in FIG. 3(B) which shows arachonidate stimulated phosphorylation of 47 kDa protein in the presence of 100 μM control and 91 kDa cytochrome b558 carboxyterminal peptides. Lane 1, no added peptide; land 2, 91 kDa cytochrome b558 carboxyterminal peptide (residue 552–570, SNSESGPRGVHFIFNKENF); land 3, as in lane 2 except 91 kDa cytochrome b558 carboxyterminal peptide added during immunoprecipitation only; lane 4, 91 kDa cytochrome b558 carboxyterminal peptide (residue 552–558 , SNSESGP); lane 5, 91 kDa cytochrome b558 carboxyterminal peptide (residue 559–570, RGVH-FIFNKENF); lane 6, 91 kDa cytochrome b558 N-terminal peptide (residue 2–9, GNWAVNEGC); lane 7, control peptide (VFSMFQGEES); lane 8, control peptide (RKRAHAG-FQATI). Furthermore, the approximate $IC_{50}$ for inhibition of $O_2^-$ production and inhibition of 47 kDa protein phosphorylation were similar (25–50 μM), suggesting that the synthetic peptide may inhibit both events by acting at a single site.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A peptide which blocks superoxide production in phagocytic cells which has 7 amino acid residues and which is from a domain of the 91 kDa subunit of human cytochrome $b_{558}$, wherein said domain is from the carboxylterminal peptide portion of the molecule.

2. The peptide of claim 1, which has the amino acid sequence Arg—Gly—Val—His—Phe—Ile—Phe.

3. A peptide as claimed in claim 1 wherein said amino acid residues further contain at least one substituent selected from a group of chemical moieties which will enhance the penetration of the peptide into phagocytic cells.

4. A peptide as claimed in claim 3 wherein the chemical moiety which will enhance the penetration of the peptide into phagocytic cells is selected from the group consisting of hydrophobic and amphophilic chemical groups.

5. A peptide as claimed in claim 4 wherein the chemical moiety which will enhance the penetration of the peptide into phagocytic cells is a cleavable esterlinked group.

6. A method for directly inhibiting activation of the specific enzyme systems involved in the oxidative burst of human phagocytic cells which comprises administering an effective amount of the peptide as claimed in claim 1 to a patient in need of such treatment.

7. A method for preventing or decreasing the tissue damage caused by phagocytic oxidative burst which comprises administering an effective amount of the peptide as claimed in claim 1 to a patient in need of such treatment.

8. A method for preventing or decreasing symptoms of diseases selected from the group consisting of gout, autoimmune disorders, myocardial infarction, adult respiratory distress syndrome, asthma and dermatological disorders which comprises administering an effective amount of the peptide as claimed in claim 1 to a patient in need of such treatment.

9. A pharmaceutical composition comprising a peptide which has 7 amino acid residues which is from a domain of the 91 kDa subunit of a human cytochrome $b_{558}$ which blocks superoxide production in phagocytic cells, wherein said domain is from the carboxyl-terminal peptide portion of the molecule; and a pharmaceutically acceptable carrier.

10. A pharmaceutical composition as claimed in claim 9, wherein the peptide has the amino acid sequence Arg—Gly—Val—His—Phe—Ile—Phe.

11. A pharmaceutical composition as claimed in claim 9, wherein the peptide has at least one substituent on the amino acid residues selected from a group of chemical moieties which will enhance the penetration of the peptide derivative into phagocytic cells.

12. A pharmaceutical composition as claimed in claim 11 wherein, the chemical moiety which will enhance the penetration of the peptide derivative into phagocytic cells is selected from the group consisting of hydrophobic and amphiphilic chemical groups.

13. A pharmaceutical composition as claimed in claim 11, wherein the chemical moiety which will enhance the penetration of the peptide derivative into phagocytic cells is a cleavable esterlinked derivative.

* * * * *